United States Patent [19]

Nolan et al.

[11] Patent Number: 4,990,523

[45] Date of Patent: Feb. 5, 1991

[54] TREATMENT OF CHRONIC INFLAMMATORY JOINT DISEASE WITH ARYLSULFONAMIDES

[75] Inventors: Joseph C. Nolan; Richard J. Barrett, both of Midlothian, Va.

[73] Assignee: A. H. Robins Company, Incorporated, Richmond, Va.

[21] Appl. No.: 367,873

[22] Filed: Jun. 19, 1989

[51] Int. Cl.$^5$ .............................................. A61K 31/41
[52] U.S. Cl. ..................................... 514/363; 514/825
[58] Field of Search ................................ 514/363, 825

[56] References Cited

PUBLICATIONS

Canad. J. Ophthal, 4:145(1969), Ferry et al., pp. 145–147.
Chemical Abstracts, 69(22):94814 (1968), (Perrine et al.).

Primary Examiner—Douglas W. Robinson
Assistant Examiner—Raymond J. Henley, III

[57] ABSTRACT

A method of treating chronic inflammatory joint disease with arylsulfonamides of the formula:

$$Z-SO_2NR^1R^2$$

wherein $R^1$ and $R^2$ are selected from hydrogen, lower alkyl, lower alkenyl, cycloalkyl, phenyl, loweralkylphenyl, 2 or 3 pyrrolidinyl, 2 or 3-(N-loweralkylpyrrolidinyl, or $R^1$ and $R^2$ taken together may form pyrrolidinyl or piperidinyl heterocyclic amino radicals and Z is an aryl group selected from substituted or unsubstituted tetrazole, 1,3,4-thiadiazole, 1,2,4-triazole, benzothiazole, benzimidazole, imidazole, pyridyl, 4,6-dimethyl pyrimidine, benzene or naphthalene is disclosed.

4 Claims, No Drawings

TREATMENT OF CHRONIC INFLAMMATORY JOINT DISEASE WITH ARYLSULFONAMIDES

BACKGROUND OF THE INVENTION

1. Field of Invention

The present invention is concerned with the use of certain arylsulfonamides in the treatment of joint disease associated with chronic arthritis methods and pharmaceutical compositions therefore. In particular the invention is concerned with internal administration of certain arylsulfonamides to arthritic mammals for the purpose of inhibiting joint degeneration.

A major consequence of chronic inflammatory joint disease (rheumatoid arthritis) and degenerative arthritis (osteoarthritis) is loss of function of those affected joints. This loss of function is due to destruction of the major structural components of the joint, cartilage and bone, and subsequent loss of the proper joint anatomy. Destruction of the architecture of the joint is due to a complex interaction of cells and mediators found in the synovial fluid, synovial membrane, bone and cartilege of the joint. In the case of rheumatoid arthritis, the inflamed synovium thickens, forms a pannus, and this invading pannus erodes the underlying cartilage and bone. In osteoarthritis, destruction appears to be mediated by the bone and cartilage cells themselves. In either case, as a consequence of chronic disease, joint destruction ensues and can lead to irreversible and permanent damage to the joint and loss of function.

2. Information Disclosure Statement

Heretofore it has not been recognized in the arts of pharmacology and medicine that arylsulfonamides have utility in treatment of joint deterioration associated with chronic arthritis.

Clinical tests administering acetazolamide percutaneously for treatment of painful cellulitic edema to patients of several types, including some afflicted with degenerative joint disease, have been reported by Marc de Seze, et al in Sem. Hop. Paris Ther. 53(2)91–94(1977). Certain improvements to cellulalgia or inflammatory cellulitis conditions were noted; however, there is no teaching or evidence presented that acetazolamide was used to treat degenerating joints or that it could be used for that indication.

A number of the arylsulfonamides useful in the method of invention are disclosed in several patents as referred to hereinbelow in description of various aspects and scope of the method of the present invention and for reference to preparation of the compounds, which patents, namely U.S. Pat. Nos. 2,608,507, 2,554,816, 2,721,204, 2,783,241, 2,835,702, 2,980,679 and British Pat. No. 795,174 are all hereby incorporated by reference.

OBJECTS AND SUMMARY OF THE INVENTION

This invention is based on the discovery that certain arylsulfonamides have utility for inhibiting damage to bone and joints in mammals suffering from chronic arthritis. In the test procedure used chronic arthritis in rats is established by administering Freund's adjuvant into a hind foot and thereafter observing the effect of administration of arylsulfonamides on joint structure by means of x-ray photography and measurement of hind paw volumes. Illustrative of compounds useful in the method of treatment of this invention, but not limited thereto are: acetazolamide, methazolamide, ethoxzolamide, benzolamide, dichlorphenamide, probenecid, and generic relatives of all. A particularly useful compound for the instant method is acetazolamide. It is therefore a primary object of the invention to provide a method of treating joint degeneration including alleviating and preventing joint degeneration associated with chronic arthritis in living animals by internally administering certain arylsulfonamides.

Another object is to use the arylsulfonamides in pharmaceutical compositions for treating, alleviating and preventing joint degeneration in living animals.

Still other objects will become apparent to one skilled in the arts of pharmacology and medicine.

DETAILED DESCRIPTION OF THE INVENTION

A general class of compounds found to have capability of inhibiting joint degeneration in arthritic animals is that of aromatic sulfonamides. The structure of this group is generally expressed by the formula:

$$Z-SO_2NR^1R^2 \qquad \text{Formula 1}$$

wherein $R^1$ and $R^2$ are selected from hydrogen, loweralkyl, loweralkenyl, cycloalkyl, phenyl, loweralkylphenyl, 2 or 3-pyrrolidinyl, 2 or 3-(N-loweralkyl)-pyrrolidinyl or $R^1$ and $R^2$ taken together with nitrogen may form pyrrolidinyl or piperidinyl heterocylic amino radicals;

Z is an aryl group selected from:

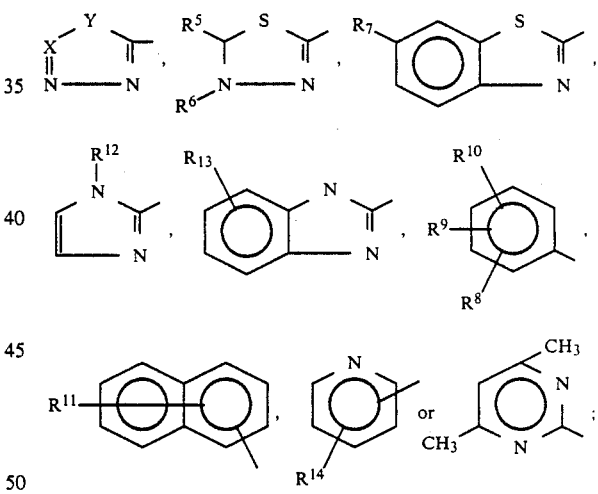

X is N or $CR^3$;
Y is S or $NR^4$;
and X, Y may be part of a fused ring system in which the 5-membered ring containing X and Y forms a ring fused with a 6-membered heterocyclic ring such as pyridine;

$R^3$ is selected from
hydrogen,
aminosulfonyl,
loweralkylcarbonylamino
2-haloacetylamino,
2-trihaloacetylamino,
phenylcarbonylamino,
phenylsulfonylamino
p-acetylaminophenylsulfonylamino,
halophenylsulfonylamino,
dihalophenylsulfonylamino, p-aminophenylsulfonylamino,
toluylsulfonylamino or
2-acetylamino-1,3,4-thiadiazoylsulfonylamino;

$R^4$ is selected from hydrogen, phenyl, loweralkyl, phenylloweralkyl or pyrido;

$R^5$ is selected from
acetylimino,
2-haloacetylimino,
2-trihaloacetylimino,
or phenylcarbonylimino;

$R^6$ is selected from
hydrogen
loweralkyl
or phenylloweralkyl;

$R^7$ is selected from hydrogen, loweralkyl, loweralkoxy or acetamido;

$R^8$, $R^9$ and $R^{10}$ are selected from
hydrogen,
nitro,
amino,
halo,
loweralkyl,
hydroxy,
loweralkoxy,
aminoloweralkyl,
—$SO_2NR^1R^2$, wherein $R^1$ and $R^2$ are as defined above,
—C(O)OH,
—C(O)Oloweralkyl,
—C(O)Ophenyl,
—C(O)phenyl $R^{11}$ is selected from hydrogen, hydroxyl or loweralkyl $R^{12}$ is selected from
hydrogen,
loweralkyl,
phenyl
or phenylloweralkyl $R^{13}$ is selected from hydrogen or loweralkyl $R^{14}$ is selected from
acetylamino,
loweralkyl
or halo and the pharmaceutically acceptable salts which form as a result of acid addition to a basic amine group, when present, or metal salts of carboxy groups when present.

In the further definition of symbols in the formulas hereof and where they appear elsewere throughout the specification and in the claims, the terms have the following significance:

The term "loweralkyl" as used herein, unless otherwise specified includes straight and branched hydrocarbon chain radicals of up to eight carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has the formula O-loweralkyl.

The term "cycloalkyl" as used herein includes primarily cyclic alkyl radicals containing 3-9 carbon atoms inclusive and includes such groups as cyclopropyl, cyclobutyl, cyclopentyl, cyclohexyl, methylcyclohexyl, cycloheptyl and the like.

The term "halo" when referred to herein includes fluorine, chlorine, bromine and iodine.

The term "phenyl" when used alone or in conjunction with loweralkyl as in "phenylloweralkyl" in the general formula definition is intended to mean unsubstituted phenyl or phenyl substituted by up to three common radicals illustrated by loweralkyl, halo, nitro, and loweralkoxy with the proviso that no more than two nitro groups or one sterically hindering group illustrated by tert-butyl are present on phenyl at any one time.

this invention is further described in greater detail by the following specific examples. Structures of the compounds of the examples are illustrated in the following descriptions and in Table 1. The scope of the invention is not limited to the examples, however.

Acetazolamide (Merck Index 10th Ed—45) and benzolamide (Merck Index 9th Ed—1104) are representative of certain compounds encompassed by the structure:

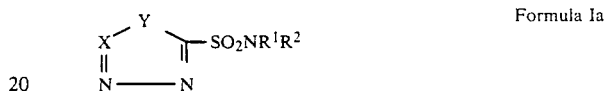

Formula Ia which compounds are encompassed by Formula 1, wherein $R^1$, $R^2$, X and Y are as defined above under Formula 1. These compounds of Formula 1a useful in the method of the present invention illustrated by the following Examples 1–21 are the subject of U.S. Pat. Nos. 2,554,816 and 2,721,204 wherein methods of preparation are described as follows:

U.S. Pat. No. 2,554,816—Examples 1–14
U.S. Pat. No. 2,721,204—Examples 15–21.
Additional illustrations are in Examples 22 and 23.

EXAMPLE NO.

1. 1,2,4-Triazole-3-sulfonamide.
2. 3-Hydroxy-4-phenyl-4,1,2-triazole-5-sulfonamide.
3. 4-Phenyl-4,1,2-triazole-3,5-disulfonamide.
4. 2-Acetylamino-1,3,4-thiadizole-5-sulfonamide, which is Acetazolamide.
5. 2-Amino-1,3-4-thiadiazole-5-sulfonamide.
6. 1,3,4-Thiadiazole-2,5-disulfonamide.
7. 2-Acetylamino-1,3-4-thiadiazole-5-sulfon-n-propylamide.
8. 2-Acetylamino-1,3,4-thiadiazole-5-sulfon-di-n-butylamide.
9. 2-Acetylamino-1,3,4-thiadiazole-5-sulfonbenzylamide.
10. 2-Acetylamino-1,3,4-thiadiazole-5-sulfon-p-toluide.
11. 1-Methyl-5-tetrazolesulfonamide.
12. 1-Phenyl-5-tetrazolesulfonamide.
13. Pyrido[2,1-c]-s-triazole-3-sulfonamide.
14. Pyrido[2,1-c]-s-triazole-3-sulfon-p-toluide.
15. 2-Benzenesulfonamido-1,3,4-thiadiazole-5-sulfonamide which is Benzolamide.
16. 2-(p-Acetylaminobenzenesulfonamido)-1,3,4-thiadiazole-5-sulfonamide.
17. 2-(p-Bromobenzenesulfonamido)-1,3,4-thiadiazole-5-sulfonamide.
18. 2-(p-Chlorobenzenesulfonamido)-1,3,4-thiadiazole-5-sulfonamide.
19. 2-(p-Toluenesulfonamido)-1,3,4-thiadiazole-5-sulfonamide.
20. 2-(3,4-Dichlorobenzenesulfonamido)-1,3,4-thiadiazole-5-sulfonamide.
21. 2-(2-Acetylamino-1,3,4-thiadiazole-5-sulfonamido)-1,3,4-thiadiazole-5-sulfonamide.

EXAMPLE 22

N-[5-(Aminosulfonyl)-1,3,4-thiadiazol-2-yl]-2-hydroxybenzamide.

Acetazolamide (50 g) was stirred and heated at reflux in 500 ml 3N hydrochloric acid for half an hour. The cooled solution was made basic with 50% sodium hydroxide. The precipitated white solid 5-amino-1,3,4-thiadiazole-2-sulfonamide was collected (Compound 1, 28 g). It was dried further at 70° C. in a vacuum oven overnight. To a mixture of Compound 1 (4.5 g, 0.025 mole) and pyridine (2.42 ml, 0.03 mole) in 70 ml acetonitrile was added acetylsalicyloyl chloride (98%, 5 g, 0.025 mole). The reaction mixture warmed and became a clear solution. Solid deposits occurred slowly after stirring at room temperature for ½ hour. After two hours the solvent was evaporated; the residue was triturated with isopropyl alcohol/water for two hours and then filtered, rinsed in succession with isopropyl alcohol/water, isopropyl alcohol/isopropyl ether, 2×isopropyl ether. From the combined mother liquor and rinsings, a second crop was collected. Both the first and second crops were combined and dissolved in 50 ml N-methyl-2-pyrrolidone. The solution was filtered and the filtrate was treated with 15 ml 3N hydrochloric acid at 70° C. for half an hour. Upon dilution with 200 ml water, a white solid precipitated. The solid was collected, rinsed with water, and dried in a vacuum over at 80° C. overnight to 4.4 g of title compound, mp>250° C.

Analysis: Calculated for $C_9H_8N_4O_4S_2$: C, 36:00; H, 2.69; N, 18.66.

Found: C, 36.92; H, 2.86; N, 18.16.

EXAMPLE 23

N-[5-(Aminosulfonyl)-1,3,4-thiadiazol-2-yl]benzamide.

Compound 1 (4.5 g, 0.025 mole) prepared in the preceding example was reacted with benzoyl chloride in the same manner as described for reaction with acetylsalicyloyl chloride in that example. The reaction mixture was concentrated and the residue was triturated in 6N hydrochloric acid. About 6 g of solid was collected by filtration and dissolved in 400 ml boiling methanol. The solution was filtered hot, and then concentrated to about half of the volume. The white solid obtained on cooling was collected, and recrystallized in methanol to give 3.08 g of white solid, mp 250° C.

Analysis: Calculated for $C_9H_8N_4O_3S_2$: C, 38.02; H, 2.84; N, 19.71.

Found: C, 38.05; H, 2.82; N, 19.64.

Methazolamide (Merck Index 10th—5824) is representative of another group of compounds encompassed by the structure:

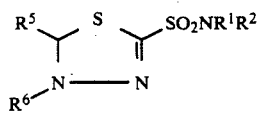

Formula Ib which compounds are encompassed by Formula 1, wherein $R^1$, $R^2$, $R^5$ and $R^6$ are as defined above under Formula 1. Preparation of compounds of Formula 1b, useful in the method of the present invention, illustrated by the following Examples 24–34 are prepared as described in U.S. Pat. No. 2,783,241.

EXAMPLE NO.

24. 5-Acetylimino-4-methyl-Δ²-1,3,4-thiadiazoline-2-sulfonamide which is methazolamide.
25. 5-Acetylimino-4-benzyl-Δ²-1,3,4-thiadiazoline-2-sulfonamide.
26. 5-Acetylimino-4-ethyl-Δ²-1,3,4-thiadiazoline-2-sulfonamide.
27. 5-Propionylimino-4-methyl-Δ²-1,3,4-thiadiazoline-2-sulfonamide.
28. 5-Propionylimino-4-ethyl-Δ²-1,3,4-thiadiazoline-2-sulfonamide.
29. 5-Formylimino-4-methyl-Δ²-1,3,4-thiadiazoline-2-sulfonamide.
30. 5-Butyrylimino-4-methyl-Δ²-1,3,4-thiadiazoline-2-sulfonamide.
31. 5-Butyrylimino-4-benzyl-Δ²-1,3,4-thiadiazoline-2-sulfonamide.
32. 5-Acetylimino-4-p-nitrobenzyl-Δ²-1,3,4-thiadiazoline-2-sulfonamide.
33. 5-Acetylimino-4-butyl-Δ²-1,3,4-thiadiazoline-2-sulfonamide.
34. 5-Propionylimino-4-butyl-Δ²-1,3,4-thiadiazoline-2-sulfonamide.

Ethoxzolamide (Merck Index 10th Ed.—3704) is representative of another group of compounds encompassed by the structure:

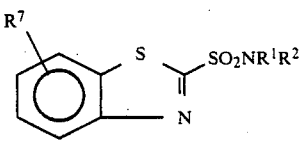

Formula Ic which compounds are encompassed by Formula 1 wherein $R^1$, $R^2$ and $R^7$ are as defined above under Formula 1. Preparation of compounds of Formula Ic useful in the method of the present invention illustrated by the following Examples 35–36 are prepared as described in British patent specification No. 795,174.

35. 6-Ethoxy-2-benzothiazolesulfonamide which is ethoxzolamide.
36. 6-Acetamidobenzothiazole-2sulfonamide.

Dichlorphenamide (Merck Index 10th Ed.—3062) and Probenecid (Merck Index 10th Ed.—7656) are representative of compounds encompassed by the structure:

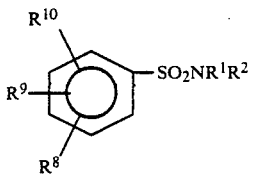

Formula Id which compounds are encompassed by Formula 1, and wherein $R^1$, $R^2$, $R^8$, $R^9$ and $R^{10}$ are as defined under Formula 1. Preparation of compounds of the dichlorphenamide type, i.e. having two fulonamide groups as in the following examples 37 and 38, are described in U.S. Pat. No. 2,835,702.

37. 4,5-Dichlorobenzene-1,3-disulfonamide.
38. 5-Bromo-4-chlorobenzene-1,3-disulfonamide which is Dichlorphenamide.

Other disulfonamides were prepared as described below, e.g. Examples 77 and 78.

The preparation of compounds of Formula 1d bearing a carboxylic acid group on phenyl are described in U.S. Pat. No. 2,608,507. These and other compounds of Formula 1d in the following examples were purchased or prepared. Reference to a company are to purchase of the compound from that company.

39. 4-N,N-Diethylsulfamyl benzoic acid, mp 195°–196° C.
40. 4-Di-n-butylsulfamyl benzoic acid, mp 160°–162° C.
41. N,N-Di-n-propyl-3-nitro-4-toluenesulfonamide, mp 54°–56° C.
42. 3-Amino-4-toluenesulfonyl piperidine, mp 117°–119° C.
43. N-Cyclohexyl-3-nitro-4-tolylsulfonamide, mp 96°–97° C.
44. 2-Nitro-4-N,N-di-n-propylsulfamylbenzoic acid, mp 152°–154° C.
45. 2-Amino-4-di-n-propylsulfamylbenzoic acid, 196°–197.5° C.
46. N-Allyl-3-nitro-4-toluenesulfonamide, mp 72°–73° C.
47. 3-Nitro-4-toluenesulfonamide, mp 144°–145° C.
48. 3-Amino-4-toluenesulfonamide, mp 175°–176° C.
49. 4-(Di-n-propylsulfamyl)-salicylic acid, mp 122°–123° C.
50. N,N-Dimethyl-3-nitro-4-toluenesulfonamide, mp 90°–91.5° C.
51. N-Isopropyl-3-nitro-4-toluenesulfonamide, mp 72°–73.5° C.
52. 3-N-Acetamido-4-toluenesulfonamide, mp 231°–232° C.
53. 3-Hydroxy-4-toluenesulfonamide, 194°–196° C.
54. N',N'-Dimethyl-3-amino-4toluenesulfonamide, mp 172°–174° C.
55. Cyclohexyl-3-amino-4-toluenesulfonamide hydrochloride, mp 91°–92.5° C.
56. 2-Amino-4-isopropylsulfamylbenzoic acid, mp 218°–220° C.
57. 4-Isopropylsulfamyl-salicyclic acid, mp 195°–197° C.
58. 4-Carboxy-3-nitrobenzenesulfonamide, mp 192.5°14 196° C.
59. N-(1-Ethyl-3-pyrrolidinyl)-4-toluenesulfonamide hydrochloride, mp 123°–125° C.
60. N,N-Di-n-butyl-4-pentyl-benzenesulfonamide.
60. 5-Aminosulfonyl-2-methoxybenzoic acid, mp 218°–220° C.
62. 5-Aminosulfonyl-2-methoxybenzoic acid, ethyl ester, mp 147°–149.5° C.
63. 4-[(Dipropylamino)sulfonyl]benzoic acid which is Propenecid.
64. 4-Amino-benzenesulfonamide.
65. Benzenesulfonamide, mp 151°–153° C.; Aldrich Chem. Co. Inc.
66. 4-Methylbenzenesulfonamide mp 136°–138° C.; Aldrich Chem Co. Inc.
67. 4-Nitrobenzenesulfonamide, mp 163°–165° C.; Aldrich Chem. Co. Inc.
68. 4-Chlorobenzenesulfonamide, mp 144°–146° C., Aldrich Chem. Co. Inc.
69. 2-Aminobenzenesulfonamide, mp 150°14 153° C.; Aldrich Chem. Co. Inc.
70. N,4-Dimethylbenzenesulfonamide, mp 76°14 79° C.; Aldrich Chem. Co. Inc.

EXAMPLE 71

3-Benzoylbenzenesulfonamide

A mixture of 9.9 g (0.05 mole) of 3-aminobenzophenone, 100 ml of acetic acid and 11 ml of concentrated hydrochloric acid and 20 g of ice was diazotized at 5°–10° C. by the dropwise addition of 3.5 g (0.05 mole) of sodium nitrate in 5 ml of water over a 30-minute period. The diazotized solution was added to approximately 25 g of sulfur dioxide in 100 ml of acetic acid containing 1 g of $CuCl_2$ in 5 ml of water. The mixture was stirred for 2 hours, the diluted with 300 ml of water. The black oil was separated by decanting the aqueous layer and the oil was dissolved in acetone. The acetone solution was treated with 100 ml of concentrated ammonium hydroxide then concentrated on a rotovaporator to remove acetone, leaving a brown precipitate in the concentrated ammonium hydroxide. This brown precipitate was collected and recrystallized from isopropyl alcohol to give 8.7 g (67%) of title compound as tan plates, mp 150.5°–152° C.

Analysis: Calculated for $C_{13}H_{11}NO_3S$: C, 59.76; H, 4.24; N, 5.36.

Found: C, 59.87; H, 4.28; N, 5.37.

EXAMPLE 72

5-(Aminosulfonyl)-2-hydroxybenzoic acid

A mixture of 2-methoxy-5-sulfamoylbenzoic acid (58 g, 0.25 mole), 48% hydrobromic acid (150 ml), and acetic acid (150 ml) was heated to reflux for five hours. The progress of reaction was checked by thin layer chromatography (silica gel, 7:2:1 ethylacetate/methanol/29% ammonium hydroxide). Upon cooling, a solid crystallized out which was collected by filtration, and rinsed with cold water. This solid was dissolved in hot water (≦85° C.) and filtered through Celite ® and recrystallized from the cool filtrate. Some of the recrystallized material was crystallized once more by dissolving in methanol, filtering, and mixing with excess amount of 1,1,1-trichloroethane. The mixture was evaporated to remove most of the methanol, and the resulting crystallizing mixture was stirred in ice bath. The solid was collected by filtration and rinsed with 1,1,1-trichloroethane, vacuum pumped at room temperature overnight to give a white solid, mp 234°–235° C.

Analysis: Calculated for $C_7H_7NO_5S$: C, 38.71; H, 3.25; N, 6.45.

Found: C, 38.53; H, 3.19; N, 6.41.

EXAMPLE 73

2-(Acetyloxy)-5-(aminosulfonyl)benzoic acid hemihydrate 5-(Aminosulfonyl)-2-hydroxybenzoic acid (9.35 g, 0.043 mole) was suspended in 50 ml acetonitrile. Pyridine (4.04 ml, 0.05 mole) was added with stirring. The resulting solution was chilled in an ice bath. Acetylchloride (3.63 ml, 0.05 mole) was added dropwise in two minutes and the reaction mixture was stirred at room temperature for four hours. To the reaction mixture was added about 50 ml each of ethyl acetate and sodium chloride solution. The organic layer was separated and extracted once more with sodium chloride solution. The aqueous layers were back extracted with acetonitrile-ethyl acetate. The organic layers were combined, dried over sodium sulfate, filtered, and concentrated to a white solid. The solid was triturated in ethyl acetate and isopropyl ether with small amount of acetonitrile overnight. The solid was collected, rinsed and dried under vacuum pump pressure to give 5.03 g of title compound, mp 179°–181° C.

Analysis: Calculated for $C_9H_9NO_6S.0.5\ H_2O$: C, 40.30; H, 3.76; N, 5.22.

Found: C, 40.95; H, 3.45; N, 5.48.

EXAMPLE 74

4-(Aminosulfonyl)benzoic acid methyl ester

A slurry of 30.2 g (0.15 mole) of p-carboxybenzenesulfonamide in 500 ml of methanol was treated with 30 g of anhydrous hydrogen chloride and the mixture was heated at reflux temperature for 3 hr. The solution was concentrated under vacuum to give 32.3 g of white, crystalline residue. A 5.0 g portion of this residue was recrystallized from 25 ml of methanol to give 3.3 g of title compound as a white powder, mp 174°–178° C.

Analysis: Calculated for $C_8H_9NO_4S$: C, 44.65; H, 4.22; N, 6.51.

Found: C 44.80; H, 4.30; N, 6.47.

EXAMPLE 75

4-(Aminosulfonyl)benzoic acid ethyl ester

A slurry of 10.0 g (0.05 mole) of p-carboxybenzenesulfonamide in 200 ml of absolute ethanol was treated with 10 g of anhydrous hydrogen chloride and heated at reflux for 5 h to give, after crystallization from ethyl acetate/petroleum ether, 10.6 g (93%) of white powder, mp 102°–104° C.

Analysis: Calculated for $C_9H_{11}NO_4S$: C, 47.15; H, 4.84; N, 6.11.

Found: C, 47.06; H, 4.89; H, 6.08.

EXAMPLE 76

4-(Aminosulfonyl)benzoic acid pentyl ester

A slurry of 32.1 g (0.15 mole) of p-carboxybenzenesulfonamide, methyl ester in 400 ml of n-pentanol was treated with 25 g of anhydrous hydrogen chloride and the mixture was heated at reflux temperature for 4 hr. The reaction was again treated by the slow addition of anhydrous hydrogen chloride during 8 hr of slow distillation. Approximately 150 ml of distillate was collected. The distillate was replaced in the reaction mixture with 150 ml of n-pentanol and the solution was heated at reflux for 66 hr. Excess pentanol and hydrogen chloride were removed by distillation under vacuum. The residue wad crystallized from a mixture of 350 ml of ethyl acetate and 500 ml of petroleum ether to give 22.0 g (54%) of white flakes, mp 96°–98° C.

Analysis: Calculated for $C_{12}H_{17}NO_4S$: C, 53.12; H, 6.32; N, 5.16.

Found: C, 53.00; H, 6.41; N, 5.19.

EXAMPLE 77

N-(1-Methylethyl)-1,4-benzenedisulfonamide

The reaction flask was charged with 7.1 g (0.12 mole) of isopropylamine in 50 ml methylene chloride. A 10 g (0.039 mole) sample of 4-(sulfonyl)benzenesulfonyl chloride prepared by a procedure described in J. Med. Chem., Vol. 6, pp. 307–11 (1963) was added in small portions allowing the temperature to rise uncontrolled. The mixture was stirred at room temperature for three hours then concentrated to a thick residue. The residue was slurried with 50 ml water to give a white solid. The solid was collected and dried. The weight of solid obtained was 5.4 g (50% yield), mp 165°–168° C. A recrystallization from 190 proof ethanol (3 ml/g) and water (3 ml/g) gave 5.0 g of title compound, mp 166°–168° C.

Analysis: Calculated for $C_9H_{14}N_2O_4S_2$: C, 38.84; H, 5.07; N, 10.06.

Found: C, 38.88; H, 5.00; N, 10.04.

EXAMPLE 78

N-Butyl-1,4-benzenedisulfonamide

The reaction flask was charged with 10 g (0.039 mole) of 4-(sulfonyl)benzenesulfonyl chloride prepared by a procedure described in J. Med. Chem., 6 pp. 307–11 (1963) in 7 ml acetonitrile. A dropping funnel was charged with 8.8 g (0.12 mole) of butylamine and the amine was added dropwise, allowing the temperature to rise. The mixture was stirred for three hours and then concentrated to a thick residue. The residue was slurried with 100 ml water and the mixture filtered to collect a white solid. After drying, the weight of solid was 8.0 g (70% yield), mp 164°–167° C. A recrystallization from 190 proof ethanol (4 ml/g) and water (4 ml/g) gave 6.6 g of title compound, mp 170°–172° C.

Analysis: Calculated for $C_{10}H_{16}N_2O_4S_2$: C, 41.08; H, 5.52; N, 9.58.

Found: C, 41.01; H, 5.40; N, 9.46.

Compounds of Formula 1 wherein Z has the structure:

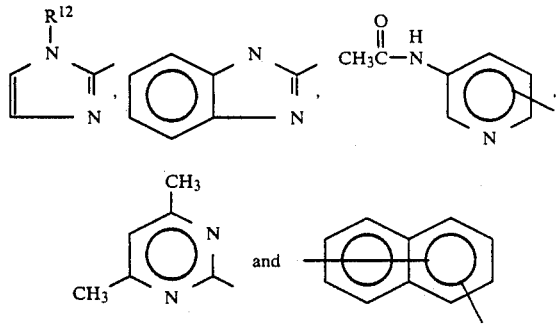

are illustrative prepared by the procedures of U.S. Pat. No. 2,980,679 and are represented in Examples 79–82 as follows:

Example 79. 1-Phenylimidazole-2-sulfonamide.
Example 80. Benzimidazole-2-sulfonamide.
Example 81. 5-Acetylamino-pyridine-2-sulfonamide.
Example 82. 4,6-Dimethyl-pyrimidine-2-sulfonamide.
Example 83. 5-Hydroxy-1-naththalenesulfonamide, m.p. 255–257 was purchased from Aldrich Chem. Co.

TABLE 1

$Z-SO_2NR^1R^2$

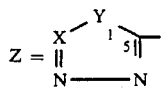

TABLE 1-continued

Z—SO$_2$NR$^1$R$^2$

| Example No. | X | Y | R$^1$ | R$^2$ |
|---|---|---|---|---|
| 1 | —CH— | —N— | H | H |
| 2 | —C(OH)— | —N(C$_6$H$_5$)— | H | H |
| 3 | —C(SO$_2$NH$_2$)— | —N(C$_6$H$_5$)— | H | H |
| 4 | —C[N—C(O)CH$_3$]— | —S— | H | H |
| 5 | —C(NH$_2$)— | —S— | H | H |
| 6 | —C(SO$_2$NH$_2$)— | —S— | H | H |
| 7 | —C[N—C(O)CH$_3$]— | —S— | —C$_3$H$_7$ | H |
| 8 | —C[N—C(O)CH$_3$]— | —S— | —C$_4$H$_9$ | H |
| 9 | —C[N—C(O)CH$_3$]— | —S— | —CH$_2$C$_6$H$_5$ | H |
| 10 | —C[N—C(O)CH$_3$]— | —S— | 4-CH$_3$—C$_6$H$_5$ | H |
| 11 | —N— | —N(CH$_3$)— | H | H |
| 12 | —N— | —N(C$_6$H$_5$)— | H | H |
| 13 | X—Y = pyridine (C N) | | H | H |
| 14 | X—Y = pyridine (C N) | | 4-CH$_3$—C$_6$H$_5$— | H |
| 15 | —C(SO$_2$NHC$_6$H$_5$)— | —S— | H | H |
| 16 | —C{SO$_2$NH[4-NHC(O)CH$_3$—C$_6$H$_4$]}— | —S— | H | H |
| 17 | —C[SO$_2$NH(4-Br—C$_6$H$_4$)]— | —S— | H | H |
| 18 | —C[SO$_2$NH(4-Cl—C$_6$H$_4$)]— | —S— | H | H |

TABLE 1-continued

| | Z—SO$_2$NR$^1$R$^2$ | | | |
|---|---|---|---|---|
| 19 | —C—<br>\|<br>SO$_2$NH(4-CH$_3$—C$_6$H$_4$) | —S— | H | H |
| 20 | —C—<br>\|<br>SO$_2$NH[3,4-(Cl)$_2$—C$_6$H$_3$] | —S— | H | H |
| 21 | 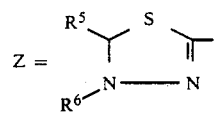 | —S— | H | H |
| 22 | —C—<br>\|<br>NHC(O)—(2-OH—C$_6$H$_4$) | —S— | H | H |
| 23 | —C—<br>\|<br>NHC(O)—C$_6$H$_5$ | —S— | H | H |

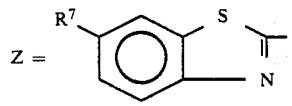

| Example No. | R$^5$ | R$^6$ | R$^1$ | R$^2$ |
|---|---|---|---|---|
| 24 | CH$_3$C(O)N= | CH$_3$— | H | H |
| 25 | CH$_3$C(O)N= | C$_6$H$_5$CH$_2$— | H | H |
| 26 | CH$_3$C(O)N= | C$_2$H$_5$— | H | H |
| 27 | C$_2$H$_5$C(O)N= | CH$_3$— | H | H |
| 28 | C$_2$H$_5$C(O)N= | C$_2$H$_5$— | H | H |
| 29 | HC(O)N= | CH$_3$— | H | H |
| 30 | C$_3$H$_7$C(O)N= | CH$_3$ | H | H |
| 31 | C$_3$H$_7$C(O)N= | C$_6$H$_5$CH$_2$— | H | H |
| 32 | CH$_3$C(O)N= | 4-NO$_2$—C$_6$H$_4$— | H | H |
| 33 | CH$_3$C(O)N= | C$_4$H$_9$ | H | H |
| 34 | C$_2$H$_5$C(O)N= | C$_4$H$_9$ | H | H |

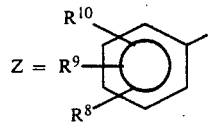

| Example No. | R$^7$ | R$^1$ | R$^2$ |
|---|---|---|---|
| 35 | C$_2$H$_5$O— | H | H |
| 36 | CH$_3$C(O)NH | H | H |

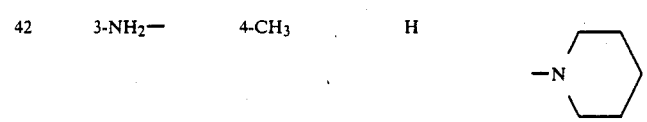

| Example No. | R$^8$ | R$^9$ | R$^{10}$ | R$^1$ | R$^2$ |
|---|---|---|---|---|---|
| 37 | 3-SO$_2$NH$_2$ | 4-Cl | 5-Cl | H | H |
| 38 | 3-SO$_2$NH$_2$ | 5-Br | 4-Cl | H | H |
| 39 | 4-COOH | H | H | C$_2$H$_5$— | C$_2$H$_5$— |
| 40 | 4-COOH | H | H | C$_4$H$_9$— | C$_4$H$_9$— |
| 41 | 3NO$_2$— | 4-CH$_3$ | H | C$_3$H$_7$— | C$_3$H$_7$— |
| 42 | 3-NH$_2$— | 4-CH$_3$ | H | —N(piperidine) | |
| 43 | 3-NO$_2$— | 4-CH$_3$ | H | C$_6$H$_{11}$— | H |
| 44 | 4-COOH | 3-NO$_2$ | H | C$_3$H$_7$— | C$_3$H$_7$— |
| 45 | 4-COOH | 3-NH$_2$ | H | C$_3$H$_7$— | C$_3$H$_7$— |
| 46 | 4-CH$_3$ | 3-NO$_2$ | H | CH$_2$=CHCH$_2$— | H |
| 47 | 4-CH$_3$ | 3-NO$_2$ | H | H | H |
| 48 | 4-CH$_3$ | 3-NH$_2$ | H | H | H |
| 49 | 4-COOH | 3-OH | H | C$_3$H$_7$— | C$_3$H$_7$— |
| 50 | 4-CH$_3$ | 3-NO$_2$ | H | CH$_3$— | CH$_3$— |
| 51 | 4-CH$_3$ | 3-NO$_2$ | H | —CH(CH$_3$)$_2$ | H |

TABLE 1-continued

Z—SO$_2$NR$^1$R$^2$

| Example | | | | R$^1$ | R$^2$ |
|---|---|---|---|---|---|
| 52 | 4-CH$_3$ | 3-NHC(O)CH$_3$ | H | H | H |
| 53 | 4-CH$_3$ | 3-OH | H | H | H |
| 54 | 4-CH$_3$ | 3-NH$_2$ | H | CH$_3$— | CH$_3$— |
| 55 | 4-CH$_3$ | 3-NH$_3$$^+$ CL$^-$ | H | C$_6$H$_{11}$— | H |
| 56 | 4-COOH | 3-NH$_2$ | H | —CH(CH$_3$)$_2$ | H |
| 57 | 4-COOH | 3-OH | H | —CH(CH$_3$)$_2$ | H |
| 58 | 4-COOH | 3-NO$_2$ | H | H | H |
| 59 | 4-CH$_3$ | H | H | (see structure below) | H |

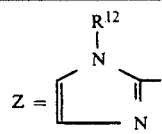

| 60 | 4-(CH$_2$)$_4$CH$_3$ | H | H | C$_4$H$_9$— | C$_4$H$_9$— |
| 61 | 3-COOH | 4-OCH$_3$ | H | H | H |
| 62 | 3-COOC$_2$H$_5$ | 4-OCH$_3$ | H | H | H |
| 63 | 4-COOH | H | H | C$_3$H$_7$— | C$_3$H$_7$— |
| 64 | 4-NH$_2$ | H | H | H | H |
| 65 | H | H | H | H | H |
| 66 | 4-CH$_3$ | H | H | H | H |
| 67 | 4-NO$_2$ | H | H | H | H |
| 68 | 4-Cl | H | H | H | H |
| 69 | 2-NH$_2$ | H | H | H | H |
| 70 | 4-CH$_3$ | H | H | CH$_3$— | H |
| 71 | 3-C(O)C$_6$H$_5$ | H | H | H | H |
| 72 | 3-COOH | 4-OH | H | H | H |
| 73 | 3-COOH | 4-OC(O)CH$_3$ | H | H | H |
| 74 | 4-COOCH$_3$ | H | H | H | H |
| 75 | 4-COOC$_2$H$_5$ | H | H | H | H |
| 76 | 4-COOC$_5$H$_{11}$ | H | H | H | H |
| 77 | 4-SO$_2$NH$_2$ | H | H | —CH(CH$_3$)$_2$ | H |
| 78 | 4-SO$_2$NH$_2$ | H | H | —C$_4$H$_9$ | H |

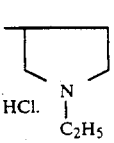

| Example No. | R$^{12}$ | R$^1$ | R$^2$ |
|---|---|---|---|
| 79 | —C$_6$H$_5$ | H | H |

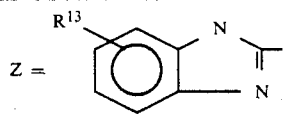

| Example No. | R$^{13}$ | R$^1$ | R$^2$ |
|---|---|---|---|
| 80 | H | H | H |

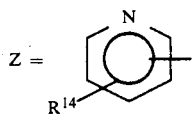

| Example No. | R$^{14}$ | —SO$_2$NR$^1$R$^2$ Position | R$^1$ | R$^2$ |
|---|---|---|---|---|
| 81 | 5-NHC(O)CH3 | 2 | H | H |

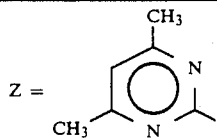

| Example No. | R$^1$ | R$^2$ |
|---|---|---|
| 82 | H | H |

TABLE 1-continued

| | | Z—SO$_2$NR$^1$R$^2$ | | |
|---|---|---|---|---|
| Example No. | R$^{11}$ | —SO$_2$NH$_2$ Position | R$^1$ | R$^2$ |
| 83 | 5-OH | 1 | H | H |

PHARMACOLOGICAL TEST PROCEDURES

Test Procedure For Assessing Joint Damage in Chronic Arthritic Rats

Adjuvant arthritis in female Lewis Wistar rats was induced using a modification of the method reported by Walz, D.T. et al. in J. Pharmac. Exp. Ther. 178, 223–231 (1971) by injection of 0.05 ml of a suspension of 1.5% dead Mycobacterium butyricum in mineral oil into the subplantar surface of the right hand paw. On Day 18 after adjuvant injection, the limb volumes of both hind limb were determined. Rats with significant swelling of the uninjected hind limbs (<2.3 ml, volume measured by mercury displacement) were randomized into groups of seven. Subsequent determinations of paw edema and x-ray scores were made on the uninjected hind limb. The rats were dosed orally daily beginning on Day 18 and continuing through Day 50 (excluding week-ends) after adjuvant injection with vehicle (0.5% Tween ® 80, 10 ml/kg) or with vehicle and test drug.

Limb volumes were also recorded on Days 29 and 50 after adjuvant injection and edema determined by volume difference compared to Day 18. The uninjected hind limb on each rat was x-rayed on Day 50 and the joint damage assayed on an arbitrary scale of 1 to 10(1=no damage, 10=maximum damage). Data on differences between control and treated groups (Day 29 edema, Day 50 edema and Day 50 x-ray scores) were analyzed by using the Dunnett's t-test (Dunnett, C.W. in J. Amer. Stat. Assoc. 50:1096–121, 1955). Results for representative compounds of Formula 1 are given in Table 2. The results indicate that the compounds given once daily to arthritic rats produce consistent, significant anti-inflammatory activity (decreases in edema and decreases in x-ray score) when given at does of 3.16 mg/kg or higher.

TABLE 2

Effect of Formula I Compounds In Adjuvant-induced Arthritis(a) in Female Lewis Wistar Rats

| Compound + Vehicle | Dose mg/kg, orally | Edema Day 29(b) | Edema Day 50(b) | X-Ray Score (mean) | Number of Animals |
|---|---|---|---|---|---|
| Control (Vehicle alone) | — | 0.19 | −0.05 | 8.57 | 55 |
| Acetazolamide | 3.16 | −0.21* | −0.42* | 6.30* | 28 |
| | 10.00 | −0.32* | −0.53* | 6.37* | 35 |
| | 31.6 | −0.43* | −0.69* | 6.79* | 7 |
| Methazolamide | 3.16 | −0.24* | −0.43* | 6.71* | 7 |
| Ethoxzolamide | 1.0 | 0.03* | −0.36* | 6.89* | 7 |
| | 3.16 | −0.29* | −0.43* | 6.11* | 7 |
| Dichlorphen- | 31.6 | −0.10* | −0.34* | 7.93* | 14 |
| amide | 100.0 | −0.29* | −0.54* | 5.89* | 7 |

(a)Dosing took place daily, beginning on Day 18 after adjuvant injection and continuing through Day 50 (excluding weekends - results are presented as mean change in all experiments).
(b)Edema Day 29: Volume of Limb on Day 29 − Volume of Limb on Day 18
Edema Day 50: Volume of Limb on Day 50 − Volume of Limb on Day 18
*p < 0.05, Dunnett's T-test.

FORMULATION AND ADMINISTRATION

Compositions containing the active compounds of Formula 1 for joint disease treatment may be internally administered to a living animal body in any one of various ways, for example, orally as in capsules or tablets, parenterally in the form of sterile solutions or suspensions and in some cases intravenously in the form of sterile solutions. In forming the compositons, the active ingredient is incorporated in a suitable carrier, illustratively a pharmaceutical carrier. Suitably solid pharmaceutical carriers which are useful in formulating the compositions of this invention include starch, gelatin, glucose, magnesium carbonate, lactose, malt and the like. Liquid compositions may be prepared using water, sugar syrups, ethyl alcohol, propylene glycol, glycerine, and the like.

Advantageously, the compositions are formulated as dosage units, each unit being adapted to supply a fixed dose of active ingredients. Tablets, coated tablets, capsules, ampules and syrups are examples of preferred dosage forms. It is only necessary that the active ingredient constitutes an effective amount, i.e. such that a suitable effective dosage will be consistent with the dosage form employed. The exact dosages as well as daily dosages will of course be determined according to standard medical principles under the direction of a physician or veterinarian.

Based on animal screening tests it appears that unit dosages for humans could be employed in the range of 0.1 to 150 milligrams. The unit dosage may be given a suitable number of times daily so that the daily dosage for an adult human may vary from 0.3 to 450 milligrams. Five to 50 milligrams appears optimum per unit dose.

The active agents of the invention may be combined with other pharmacologically active agents, or with buffers, antacids or the like for administration and the proportion of the active agent in the compositions may vary widely.

Various modifications and equivalents will be apparent to one skilled in the art and may be made in the compounds, methods, processes, and pharmaceutical compositions of the present invention without departing from the spirit and scope thereof, and it is therefore to be understood that the invention is to be limited only by the scope of the appended claims.

What is claimed is:

1. A method of treating joint degeneration associated with chronic arthritis in a living animal which comprises internally administering to said animal an effective amount for treating joint degeneration associated with chronic arthritis of an arylsulfonamide having the formula:

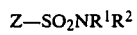

wherein
R$^1$ and R$^2$ are members selected from the group consisting of hydrogen, loweralkyl, loweralkenyl, cycloalkyl, phenyl and loweralkylphenyl;
Z is an aryl group selected from the group consisting of

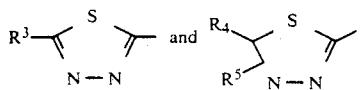

$R^3$ is a member selected from the group consisting of hydrogen, aminosulfonyl, loweralkylcarbonylamino, 2-haloacetylamino, 2-trihaloacetylamino, phenylcarbonylamino, phenylsulfonylamino, p-acetylaminophenylsulfonylamino, halophenylsulfonylamino, dihalophenylsulfonylamino, p-aminophenylsulfonylamino and toluylsulfonylamino;

$R^4$ is a member selected from the group consisting of acetylimino, 2-haloacetylimino, 2-trihaloacetylimino and phenylcarbonylimino;

$R^5$ is a member selected from the group consisting of hydrogen, loweralkyl and phenylloweralkyl; and the pharmaceutically acceptable salts which are formed as the result of an acid addition to a basic amine group, when said amine group is present or metal salts of carboxy groups when said carboxy groups are present.

2. The method according to claim 1, wherein the arylsulfonamide is acetazolamide.

3. The method according to claim 1, wherein the arylsulfonamide is benzolamide.

4. The method according to claim 1, wherein the arylsulfonamide is methazolamide.

* * * * *